(12) United States Patent
Tsujita

(10) Patent No.: US 7,620,445 B2
(45) Date of Patent: Nov. 17, 2009

(54) APPARATUS FOR ACQUIRING TOMOGRAPHIC IMAGE FORMED BY ULTRASOUND-MODULATED FLUORESCENCE

(75) Inventor: Kazuhiro Tsujita, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 122 days.

(21) Appl. No.: 11/339,526

(22) Filed: Jan. 26, 2006

(65) Prior Publication Data

US 2006/0184049 A1    Aug. 17, 2006

(30) Foreign Application Priority Data

Jan. 26, 2005    (JP)    ............................. 2005-018347

(51) Int. Cl.
*A61B 8/14*    (2006.01)
*A61B 6/00*    (2006.01)

(52) U.S. Cl. ..................... 600/476; 600/473; 600/467

(58) Field of Classification Search ................. 600/431, 600/473, 476

See application file for complete search history.

(56) References Cited

U.S. PATENT DOCUMENTS

| | | | |
|---|---|---|---|
| 5,999,836 A | 12/1999 | Nelson et al. | |
| 6,002,958 A * | 12/1999 | Godik | 600/407 |
| 6,041,248 A * | 3/2000 | Wang | 600/407 |
| 6,174,291 B1 | 1/2001 | McMahon et al. | |
| 6,245,015 B1 * | 6/2001 | Pattanayak | 600/438 |
| 6,390,978 B1 | 5/2002 | Irion et al. | |
| 6,609,015 B2 * | 8/2003 | Lucassen et al. | 600/322 |
| 6,738,653 B1 * | 5/2004 | Sfez et al. | 600/322 |
| 6,815,694 B2 * | 11/2004 | Sfez et al. | 250/492.1 |
| 6,957,096 B2 * | 10/2005 | Sfez et al. | 600/407 |
| 7,144,370 B2 * | 12/2006 | Fomitchov | 600/438 |
| 2003/0129579 A1 * | 7/2003 | Bornhop et al. | 435/4 |
| 2004/0099815 A1 * | 5/2004 | Sfez et al. | 250/492.1 |
| 2004/0197267 A1 * | 10/2004 | Black et al. | 424/9.6 |
| 2005/0107694 A1 * | 5/2005 | Jansen et al. | 600/431 |
| 2006/0058685 A1 * | 3/2006 | Fomitchov et al. | 600/476 |
| 2006/0224053 A1 * | 10/2006 | Black et al. | 600/310 |

(Continued)

FOREIGN PATENT DOCUMENTS

WO    WO 02/056670 A2    7/2002

(Continued)

OTHER PUBLICATIONS

In Vivo Endoscopic Optical Biopsy With Optical Coherence Tomography, Guillermo J. Tearney, Mark E. Brezinski, Brett E. Bouma, Stephen A. Boppart, Coastas Pitris, Jammes F. Southern and James G. Fujimoto, American Assoc. for the Advancement of Science, (Jun. 27, 1997), pp. 2037-2039.

(Continued)

*Primary Examiner*—Eric F Winakur
*Assistant Examiner*—Helene Bor
(74) *Attorney, Agent, or Firm*—Sughrue Mion, PLLC

(57) ABSTRACT

In a fluorescence tomography apparatus for obtaining fluorescence tomographic images of a region of an object to be observed: an application unit concurrently applies an ultrasonic wave and excitation light to the region so that ultrasound-modulated fluorescence is emitted from the region under the influence of the ultrasonic wave; and a first image acquisition unit acquires a fluorescence tomographic image of the region on the basis of the ultrasound-modulated fluorescence.

13 Claims, 3 Drawing Sheets

U.S. PATENT DOCUMENTS

2006/0247506 A1* 11/2006 Balberg et al. .............. 600/323
2007/0093702 A1* 4/2007 Yu et al. .................... 600/326

FOREIGN PATENT DOCUMENTS

WO 03/059150 A2 7/2003
WO WO 2006/027738 A1 3/2006

OTHER PUBLICATIONS

Jun Li, et al., "Ultrasound-modulated optical computed tomography of biological tissues", Applied Physics Letters, Mar. 1, 2004, pp. 1597-1599, vol. 84, No. 9.

S. B. Colak, et al.: "Tomographic image reconstruction from optical projections in light-diffusing media"; Applied Optics, vol. 36. No. 1; pp. 180-213; 1997.

* cited by examiner

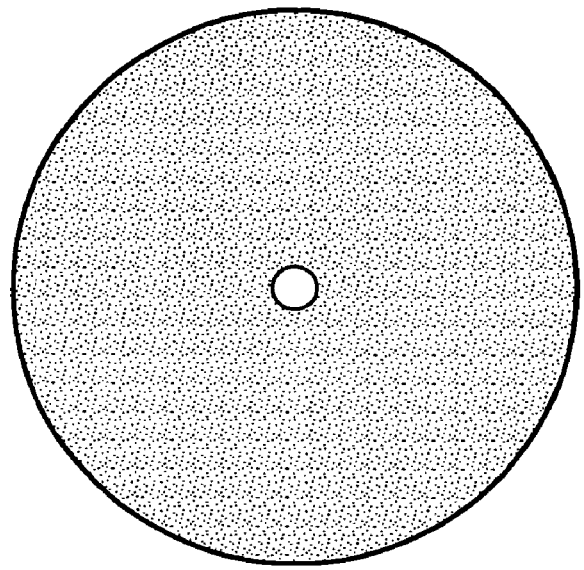

APPARATUS FOR ACQUIRING TOMOGRAPHIC IMAGE FORMED BY ULTRASOUND-MODULATED FLUORESCENCE

BACKGROUND OF THE INVENTION

1. Field of the Invention

The present invention relates to a fluorescence tomography apparatus which applies excitation light to a region of an object to be observed, detects fluorescence emitted from the object, and acquires a fluorescence tomographic image of the region.

2. Description of the Related Art

In recent years, optical tomography apparatuses which acquire tomographic images by using light have been used in the field of medical diagnosis. The optical tomography apparatuses using confocal optical systems and the optical tomography apparatuses using time-resolved measurement systems are already in actual use.

In addition, commercialization of the optical coherence tomography (OCT) apparatuses has been recently proceeding. In the OCT apparatuses, low-coherence light is emitted from a light source realized by a super luminescent diode (SLD) or the like, and split into measurement light (light applied to an object for measurement) and reference light. The frequency of the reference light or the measurement light is slightly shifted by using a piezoelectric element or the like, and the measurement light is applied to a region to be observed, so that light reflected from a position at a desired depth in the region to be observed interferes with the reference light, and information on tomography is obtained by measuring the intensity of the interference light by heterodyne interferometry. It is possible to obtain information at a depth at which the optical path length of the reference light coincides with the optical path length of the measurement light, by slightly moving a movable mirror arranged in the optical path of the reference light so as to slightly change the optical path length of the reference light.

Further, development of an ultrasound-modulated optical tomography apparatus has also been proceeding recently as disclosed in "Ultrasound-modulated Optical Computed Tomography of Biological Tissues", by Jun Li and L. V. Wang, Applied Physics Letters, Vol. 84 (2004), No. 9, pp. 1597-1599. In such an ultrasound-modulated optical tomography apparatus, an ultrasonic wave and light are concurrently applied to a region to be observed, and an ultrasound-modulated-light tomographic image is obtained on the basis of ultrasound-modulated reflected light, which is generated by reflection from the region influenced by the ultrasonic wave.

Furthermore, fluorescence tomography apparatuses using a confocal optical system are being actually used. In such fluorescence tomography apparatuses, excitation light is applied to a region to be observed, and a fluorescence tomography image is obtained by detecting fluorescence emitted from the region. Moreover, fluorescence tomography apparatuses using a time-resolved measurement system are disclosed in U.S. Pat. No. 6,174,291.

The optical tomography apparatuses using a confocal optical system can obtain high-resolution optical tomographic images. However, it is impossible to acquire a fluorescence tomographic image of a region which is to be observed and extends to a depth of 0.5 mm or greater from a surface of the region.

On the other hand, the fluorescence tomography apparatuses using a time-resolved measurement system can obtain fluorescence tomographic images of regions at depths from zero to several millimeters from a surface of the region. However, in this case, the resolution is at most approximately 1 mm, and insufficient.

In particular, in order to diagnose the extension of a lesion in the field of medicine, there are strong demands for a fluorescence tomography apparatus which can obtain a high-resolution fluorescence tomographic image of a region extending to a depth of several millimeters.

SUMMARY OF THE INVENTION

The object of the present invention is to provide a fluorescence tomography apparatus which can obtain high-resolution fluorescence tomographic images of a region extending to a depth of several millimeters.

According to the present invention, there is provided a fluorescence tomography apparatus for obtaining fluorescence tomographic images of a region of an object to be observed. The fluorescence tomography apparatus comprises: an application unit which concurrently applies a first ultrasonic wave and excitation light to the region so that ultrasound-modulated fluorescence is emitted from the region under the influence of the first ultrasonic wave; and a first image acquisition unit which acquires a fluorescence (ultrasound-modulated-fluorescence) tomographic image of the region on the basis of the ultrasound-modulated fluorescence.

The fluorescence tomography apparatus according to the present invention can obtain a fluorescence tomographic image of a region which is to be observed and extends to a depth of several millimeters from a surface of the region, with high resolution (at most tens of micrometers). This is because when an ultrasonic wave is applied to the region to be observed, the ultrasonic wave causes an elastic wave (i.e., compression and rarefaction of tissue) in the region to be observed, and produces a distribution of the refractive index in the region. When fluorescence is emitted from the region which is to be observed and is in the above situation, the fluorescence is influenced by the compressed and rarefied state of the tissue, i.e., the fluorescence is modulated. It is possible to obtain a fluorescence (ultrasound-modulated-fluorescence) tomographic image by detecting and analyzing the ultrasound-modulated fluorescence.

Preferably, the fluorescence tomography apparatus according to the present invention may also have one or any possible combination of the following additional features (i) to (iv).

(i) The ultrasound-modulated fluorescence may be autofluorescence which is emitted from the object per se, and modulated with the ultrasonic wave. Alternatively, in the case where the region to be observed is doped in advance with a fluorescent agent having an affinity for a tumor, the ultrasound-modulated fluorescence may be fluorescence which is emitted from the fluorescent agent, and modulated with the ultrasonic wave. In the latter case, it is possible to obtain information on the tumor in the region to be observed, by observing the fluorescence tomographic image, where the information may indicate the existence or absence of a tumor in the region, the position or size of the tumor, and the like.

(ii) The first image acquisition unit may comprise a three-dimensional-image generation unit which generates a three-dimensional fluorescence (ultrasound-modulated-fluorescence) tomographic image from a plurality of fluorescence (ultrasound-modulated-fluorescence) tomographic images, which are acquired by the first image acquisition unit. In this case, it is possible to observe more readily the state of the region to be observed.

(iii) The fluorescence tomography apparatus according to the present invention may further comprise: a second application unit which concurrently applies a second ultrasonic wave and first light to the region so that the first light is reflected from the region under the influence of the second ultrasonic wave, and ultrasound-modulated reflected light is generated; and a third image acquisition unit which acquires an ultrasound-modulated-light tomographic image of the region on the basis of the ultrasound-modulated reflected light. In this case, when the ultrasound-modulated-light tomographic image is displayed concurrently with the fluorescence (ultrasound-modulated-fluorescence) tomographic image, or when the ultrasound-modulated-light tomographic image is superimposed on the fluorescence (ultrasound-modulated-fluorescence) tomographic image, and the superimposed image is displayed, it is possible to concurrently observe the fluorescence emitted from the region to be observed, together with a tomographic profile of the region to be observed.

(iv) The fluorescence tomography apparatus according to the present invention may further comprise: a third application unit which applies second light to the region so that the second light is reflected from the region; and a third image acquisition unit which acquires an optical tomographic image of the region on the basis of the second light reflected from the region. In this case, it is possible to obtain a tomographic image of a near-surface portion of the region to be observed, with higher resolution.

(v) The fluorescence tomography apparatus according to the present invention may further comprise: a fourth application unit which applies a third ultrasonic wave to the region so that the third ultrasonic wave is reflected from the region; and a fourth image acquisition unit which acquires an ultrasonic tomographic image of the region on the basis of the third ultrasonic wave reflected from the region. In this case, it is possible to obtain a tomographic image of a deeper portion of the region to be observed.

BRIEF DESCRIPTION OF THE DRAWINGS

FIG. 2A is a diagram schematically illustrating an example of an optical tomographic image.

FIG. 2B is a diagram schematically illustrating an example of an ultrasound-modulated-light tomographic image.

FIG. 2C is a diagram schematically illustrating an example of a fluorescence (ultrasound-modulated-fluorescence) tomographic image.

FIG. 2D is a diagram schematically illustrating an example of an ultrasonic tomographic image.

FIG. 3 is a diagram schematically illustrating an example of a superimposed tomographic image.

DESCRIPTION OF THE PREFERRED EMBODIMENTS

A preferred embodiment of the present invention is explained in detail below with reference to drawings.

Outline of Embodiment

Figure 1:
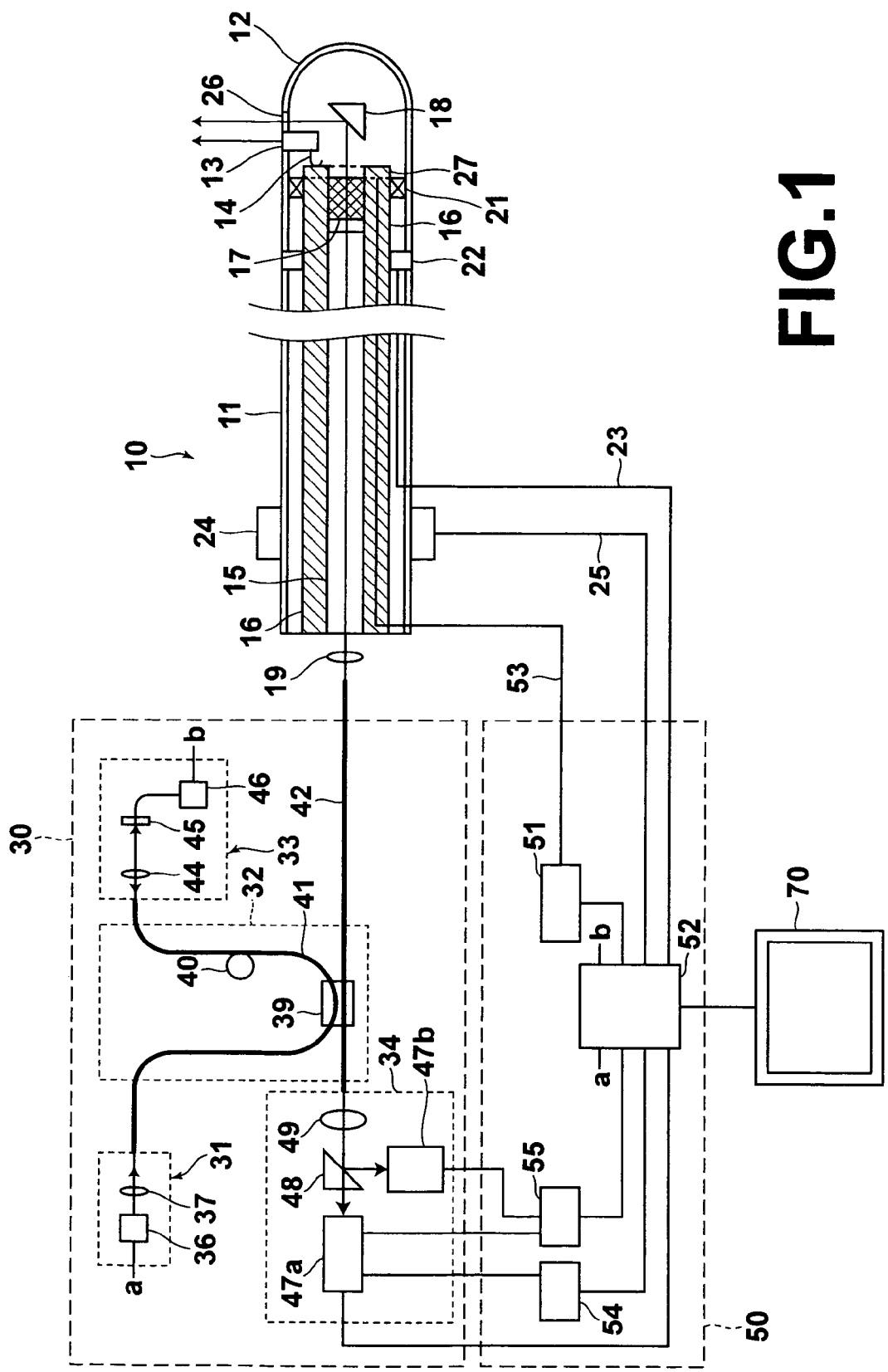
FIG. 1 is a diagram schematically illustrating the construction of a fluorescence tomography apparatus according to an embodiment of the present invention.

FIG. 1 is a diagram schematically illustrating the construction of the fluorescence tomography apparatus according to an embodiment of the present invention. The fluorescence tomography apparatus of FIG. 1 comprises a probe 10, an optical unit 30, a signal processing unit 50, and a monitor 70. The probe 10 can be inserted through a forceps channel of an endoscope, the optical unit 30 is connected to the probe 10, the signal processing unit 50 is connected to the probe 10 and the optical unit 30, and the monitor 70 is connected to the signal processing unit 50. In addition, the fluorescence tomography apparatus of FIG. 1 has a function of acquiring an optical tomographic image, a function of acquiring an ultrasonic tomographic image, a function of acquiring a fluorescence (ultrasound-modulated-fluorescence) tomographic image formed by ultrasound-modulated fluorescence, and a function of acquiring an ultrasound-modulated-light tomographic image. A (human) subject is doped in advance with a fluorescent agent having an affinity for a tumor. In this example, the fluorescent agent emits fluorescence in the wavelength range of 770 to 900 nm when the fluorescent agent is irradiated with excitation light having a wavelength of 750 nm.

The fluorescence tomography apparatus of FIG. 1 displays on a monitor an ultrasonic tomographic image, an optical tomographic image, a fluorescence (ultrasound-modulated-fluorescence) tomographic image, and an ultrasound-modulated-light tomographic image. In addition, the fluorescence tomography apparatus of FIG. 1 generates a superimposed tomographic image by superimposing a fluorescence (ultrasound-modulated-fluorescence) tomographic image and an ultrasound-modulated-light tomographic image, and displays the superimposed tomographic image on the monitor. Further, the fluorescence tomography apparatus of FIG. 1 generates a synthesized tomographic image by synthesizing an optical tomographic image, an ultrasound-modulated-light tomographic image, and an ultrasonic tomographic image, and superimposing a fluorescence (ultrasound-modulated-fluorescence) tomographic image on the image generated by the synthesis of the optical tomographic image, the ultrasound-modulated-light tomographic image, and the ultrasonic tomographic image, and then displays the synthesized tomographic image on the monitor. Furthermore, the fluorescence tomography apparatus of FIG. 1 generates a three-dimensional fluorescence (ultrasound-modulated-fluorescence) tomographic image on the basis of a plurality of successive fluorescence (ultrasound-modulated-fluorescence) tomographic images, and displays the three-dimensional fluorescence tomographic image on the monitor.

Construction for Ultrasonic Tomographic Image

First, a portion of the construction of the fluorescence tomography apparatus related to acquisition of the ultrasonic tomographic image is explained below.

In the construction of FIG. 1, the probe 10 is covered by a flexible sheath 11 and a rotatable sheath 12, which can be rotated with respect to the flexible sheath 11. An ultrasonic transducer 13 is arranged in the rotatable sheath 12. The ultrasonic transducer 13 applies an ultrasonic wave to a region of the subject to be observed (not shown), and receives a reflected ultrasonic wave (echo) generated in the region by reflection of the ultrasonic wave applied to the region. The signal processing unit 50 comprises an ultrasound-signal processing unit 51. The ultrasound-signal processing unit 51 sends to the ultrasonic transducer 13 an ultrasonic-actuation signal (an electric signal for actuating the ultrasonic transducer 13 so as to make the ultrasonic transducer 13 generate the ultrasonic wave), receives from the ultrasonic transducer 13 a reflected-ultrasound signal (an electric signal indicating the reflected ultrasonic wave), and generates ultrasonic tomographic information. In addition, the signal processing unit 50 also comprises a controller 52, which is connected with the ultrasound-signal processing unit 51. The ultrasonic transducer 13 and the ultrasound-signal processing unit 51 are connected through cables 14 and 53 and terminals 27, which is arranged around an end of an outer sheath 16 of an optical fiber 15 in the probe 10. The optical fiber 15 and the outer sheath 16 are explained later.

The cables 14 and 53 are arranged in contact with the terminals 27. That is, even when the rotatable sheath 12 rotates, the cables 14 and 53 are connected to the terminals 27 at all times. Therefore, the ultrasound-actuation signal and the reflected-ultrasound signal can be transmitted without intermission.

The ultrasound-signal processing unit 51 generates the ultrasonic tomographic information on the basis of the waveshape of the reflected-ultrasound signal (which is received from the ultrasonic transducer 13), and outputs the ultrasonic tomographic information to the controller 52. The controller 52 generates an ultrasonic tomographic image on the basis of the ultrasonic tomographic information. The controller 52 is connected to respective portions of the fluorescence tomography apparatus of FIG. 1, controls the respective portions, and generates the ultrasonic tomographic image, the optical tomographic image, the fluorescence (ultrasound-modulated-fluorescence) tomographic image, and the ultrasound-modulated-light tomographic image on the basis of the ultrasonic tomographic information, optical tomographic information, ultrasound-modulated-fluorescence tomographic information, and ultrasound-modulated-light tomographic information, respectively. Details of the operations of the controller 52 are explained later.

Details of Construction

Hereinbelow, portions of the construction of the fluorescence tomography apparatus of FIG. 1 related to acquisition of the ultrasonic tomographic image, the optical tomographic image, the fluorescence (ultrasound-modulated-fluorescence) tomographic image, and the ultrasound-modulated-light tomographic image are explained.

First, the construction of the probe 10 is explained below.

The outer sheath 16 is a flexible sheath, arranged around the optical fiber 15 and covered by the flexible sheath 11. The near-end portion of the outer sheath 16 is covered by the rotatable sheath 12, and supported by bearings so that the rotatable sheath 12 can rotate around an axis. The base edge of the rotatable sheath 12 is connected to a centerless motor 22. The centerless motor 22 has a function of a rotary encoder (a unit for detecting the rotation angle), and sends to the controller 52 through a signal line 23 a signal indicating the detected rotation angle.

A rod lens 17 and a mirror 18 are arranged at the tip of the rotatable sheath 12. The rod lens 17 condenses light guided through the optical fiber 15 so that the light converges in the region to be observed, and also condenses reflected light (light applied to and reflected from the region to be observed) or ultrasound-modulated light or ultrasound-modulated fluorescence so that the condensed light or ultrasound-modulated light or ultrasound-modulated fluorescence enters the core of the optical fiber 15. (The ultrasound-modulated light and the ultrasound-modulated fluorescence are explained later.) The mirror 18 reflects the light from the optical fiber 15, the reflected light, the ultrasound-modulated light, and the ultrasound-modulated fluorescence so that the directions of the light from the optical fiber 15, the reflected light, the ultrasound-modulated light, and the ultrasound-modulated fluorescence are changed by 90 degrees. The mirror 18 is fixed to the rotatable sheath 12, and rotates with the rotatable sheath 12. In addition, an optical window 26 is arranged at the tip of the rotatable sheath 12 so that the light from the optical fiber 15 can be outputted through the optical window 26 after the reflection by the mirror 18. Further, a condensing lens 19 is arranged on the base edge side of the optical fiber 15.

A linear actuator 24 is arranged at a portion of the flexible sheath 11 near the base edge of the flexible sheath 11 in order to move the probe 10 in the length direction of the probe 10 through the forceps channel of the endoscope. The linear actuator 24 has a function of a linear encoder (i.e., a unit for detecting the moving distance). The linear actuator 24 sends through a signal line 25 to the controller 52 a signal indicating the detected moving distance.

The aforementioned ultrasonic transducer 13 is fixed to the rotatable sheath 12 in the vicinity of the optical window 26 (at the tip of the rotatable sheath 12) so that the ultrasonic transducer 13 emits an ultrasonic wave to the region to be observed, in the direction toward which the light from the optical fiber 15 is reflected by the mirror 18. Alternatively, the ultrasonic transducer 13 maybe arranged at another position. In other words, the ultrasonic transducer 13 may be arranged at any position where a region to which the light from the optical fiber 15 is applied and a region to which the ultrasonic wave is applied overlap almost completely, and the ultrasonic transducer 13 does not interfere with the application of the light.

The optical unit 30 comprises a light-source unit 31, a fiber-coupling optical system 32, an optical-path delay unit 33, and an optical detection unit 34.

The light-source unit 31 comprises a light source 36 and a condensing lens 37. The light source 36 is realized by a super luminescent diode (SLD) or the like, and emits low-coherence light having the wavelength of 750 nm. The condensing lens 37 condenses the low-coherence light emitted from the light source 36. Thus, the light-source unit 31 outputs low-coherence light L having the wavelength of 750 nm.

The fiber-coupling optical system 32 splits the low-coherence light L outputted from the light-source unit 31, into reference light Lr and measurement light Ls, and combines the reference light Lr with reflected measurement light Ls (i.e., reflected light generated by reflection of the measurement light Ls at a certain depth in the region to be observed). The fiber-coupling optical system 32 comprises a fiber coupler 39, a piezoelectric element 40, and optical fibers 41 and 42. The fiber coupler 39 splits the low-coherence light L outputted from the light-source unit 31, into the reference light Lr and the measurement light Ls, and combines the reference light Lr with the reflected measurement light Ls'. The piezoelectric element 40 causes a slight frequency shift in the reference light Lr. The optical fiber 41 connects the light-source unit 31 with the optical-path delay unit 33 through the fiber coupler 39, and the optical fiber 42 optically connects the optical detection unit 34 with the rotatable sheath 12 through the fiber coupler 39.

The optical-path delay unit 33 is arranged in the optical path of the reference light Lr, and changes the optical path length of the reference light Lr. The optical-path delay unit 33 comprises a condensing lens 44, a reference-light mirror 45, and an actuator 46. The reference-light mirror 45 reflects the reference light Lr. The condensing lens 44 collimates the reference light Lr outputted from the optical fiber 41, and makes the reflected reference light Lr (i.e., the reference light Lr reflected by the reference-light mirror 45) enter the optical fiber 41. The actuator 46 moves the reference-light mirror 45 in the horizontal direction in FIG. 1. When the reference-light mirror 45 is moved in the horizontal direction in FIG. 1, the optical path length of the reference light Lr is changed.

The optical detection unit 34 detects the optical intensity of interference light Lc produced by interference of the reflected measurement light Ls' with the reference light Lr, and the optical intensities of the ultrasound-modulated light and the ultrasound-modulated fluorescence (which are explained later).

The optical detection unit 34 comprises optical detectors 47a and 47b, a dichroic mirror 48, and a condensing lens 49. The optical detector 47a detects the optical intensities of the interference light Lc and the ultrasound-modulated light. The dichroic mirror 48 is arranged in the stage preceding the optical detector 47a, reflects light having wavelengths equal to or greater than 765 nm toward the direction perpendicular to the incident direction of the light, and allows light having wavelengths smaller than 765 nm to pass through the dichroic mirror 48. The condensing lens 49 is arranged in the stage preceding the dichroic mirror 48. The optical detector 47b detects the optical intensity of light reflected by the dichroic mirror 48, and is provided for detecting the optical intensity of the ultrasound-modulated fluorescence (which is explained later).

The optical detector 47a is connected to an optical-tomographic-information generation unit 54, an ultrasound-modulated-tomographic-information generation unit 55, and the controller 52, and outputs the detection result to the optical-tomographic-information generation unit 54 and the ultrasound-modulated-tomographic-information generation unit 55 under control of the controller 52. The optical detector 47b is also connected to the ultrasound-modulated-tomographic-information generation unit 55.

In the signal processing unit 50, the optical-tomographic-information generation unit 54 generates optical tomographic information on the basis of the optical intensity of the interference light Lc detected by the optical detector 47a, and outputs the optical tomographic information to the controller 52. The ultrasound-modulated-tomographic-information generation unit 55 generates ultrasound-modulated-light tomographic information on the basis of the optical intensity of the ultrasound-modulated light detected by the optical detector 47a, and outputs the ultrasound-modulated-light tomographic information to the controller 52. In addition, the ultrasound-modulated-tomographic-information generation unit 55 also generates ultrasound-modulated-fluorescence tomographic information on the basis of the optical intensity of the ultrasound-modulated fluorescence detected by the optical detector 47b, and outputs the ultrasound-modulated-fluorescence tomographic information to the controller 52.

Acquisition, Generation, and Display of Tomographic Images

Hereinbelow, the operations for acquisition of the optical tomographic image, the ultrasonic tomographic image, the ultrasound-modulated-light tomographic image, and the ultrasound-modulated-fluorescence tomographic image, and generation and display of the respective types of tomographic images, the superimposed tomographic image, and the synthesized tomographic image, which are performed by the fluorescence tomographic apparatus according to the present embodiment, are explained in detail.

In order to observe a body cavity of a subject (patient), the probe 10 is inserted through the forceps channel of the endoscope, and the endoscope is inserted into the body cavity of the patient. The operator leads the tip of the endoscope to a desired position in the body cavity while observing the image displayed on the monitor of the endoscope.

First, operations for acquiring and displaying an ultrasonic tomographic image are explained below.

The ultrasound-signal processing unit 51 oscillates the ultrasound-actuation signal under control of the controller 52. The ultrasound-actuation signal propagates through the cable 53, the terminals 27, and the cable 14 to the ultrasonic transducer 13. The ultrasonic transducer 13 converts the ultrasound-actuation signal into an ultrasonic wave, which is applied to the region to be observed. The ultrasonic wave is reflected from the region to be observed, and the ultrasonic transducer 13 converts the reflected ultrasonic wave into an electric signal, which is the aforementioned reflected-ultrasound signal, and sent to the ultrasound-signal processing unit 51. The ultrasound-signal processing unit 51 generates ultrasonic tomographic information on the basis of the waveshape of the reflected-ultrasound signal, and sends the ultrasonic tomographic information to the controller 52.

In addition, the rotatable sheath 12 is rotated by driving the centerless motor 22 so as to move the direction of the emission of the ultrasonic wave, and perform radial scanning around the length axis of the optical fiber 15. At this time, a signal indicating the rotation angle detected by the aforementioned unit for detecting the rotation angle is sent to the controller 52 through the aforementioned signal line 23.

The controller 52 generates a radial ultrasonic tomographic image on the basis of the rotation angle of the centerless motor 22 and the ultrasonic tomographic information sent from the ultrasound-signal processing unit 51, and outputs the radial ultrasonic tomographic image to the monitor 70. The radial ultrasonic tomographic image is displayed on the monitor 70, for example, as illustrated in FIG. 2A.

Further, it is possible to acquire and display a linear ultrasonic tomographic image by activating the linear actuator 24 and performing linear scanning with the probe 10.

Next, operations for acquiring and displaying an optical tomographic image are explained below.

The fluorescence tomography apparatus according to the present embodiment contains an optical coherence tomography (OCT) apparatus as a unit for acquiring an optical tomographic image.

First, low-coherence light for acquisition of the optical tomographic image is outputted from the light-source unit 31 under control of the controller 52, which is connected to port "a" of the light-source unit 31 at port "a" of the controller 52. Specifically, low-coherence light is emitted from the light source 36, condensed by the condensing lens 37, and lead into the optical fiber 41. The low-coherence light which propagates through the optical fiber 41 to the fiber coupler 39 is split into the reference light Lr and the measurement light Ls. Then, the reference light Lr propagates through the optical fiber 41 to the optical-path delay unit 33, and the measurement light Ls propagates through the optical fiber 42 toward the rotatable sheath 12. The reference light Lr is modulated by the piezoelectric element 40 arranged in the path of the reference light Lr so that a slight frequency difference occurs between the reference light Lr and the measurement light Ls.

The measurement light Ls lead through the optical fiber 42 enters the optical fiber 15 through the condensing lens 19, propagates through the optical fiber 15, is outputted from the tip of the optical fiber 15, and is then applied to the region to be observed. At this time, a portion of the measurement light Ls which is reflected from a certain depth in the region to be observed (as the reflected measurement light Ls') is returned to the fiber coupler 39 through the mirror 18, the rod lens 17, the optical fiber 15, the condensing lens 19, and the optical fiber 42. Then, the reflected measurement light Ls' is combined with the reference light Lr which is modulated by the piezoelectric element 40 and returned to the fiber coupler 39 through the optical-path delay unit 33 and the optical fiber 41 as explained below.

That is, the reference light Lr modulated by the piezoelectric element 40 as mentioned before propagates through the optical fiber 41 and the condensing lens 44 in the optical-path delay unit 33, and is then incident on the reference-light mirror 45. At this time, the modulated reference light Lr is reflected by the reference-light mirror 45, returned to the fiber coupler 39 through the condensing lens 44 and the optical fiber 41, and combined with the reflected measurement light Ls' by the fiber coupler 39 as mentioned above.

Thus, the reflected measurement light Ls' and the reference light Lr modulated and reflected as above are superimposed on the identical fiber 42, and interfere, so that interference light Lc is generated by interference of the reflected measurement light Ls' with the modulated and reflected reference light Lr and outputted from the optical fiber 42. Then, the interference light Lc propagates through the condensing lens 49 and the dichroic mirror 48, and enters the optical detector 47a.

Since the reference light Lr and the reflected measurement light Ls' are low-coherence light having a small coherence distance, when the optical path length of the aforementioned portion of the measurement light Ls along the path from the fiber coupler 39 via the region (to be observed) back to the fiber coupler 39 is equal to the optical path length of the reference light Lr along the path from the fiber coupler 39 via the optical-path delay unit 33 back to the fiber coupler 39, the reference light Lr and the reflected measurement light Ls' interfere and a beat signal is generated, where the intensity of the beat signal varies at the frequency corresponding to the difference $\Delta f$ between the frequency of the reference light Lr and the frequency of the reflected measurement light Ls'.

The optical detector 47a detects the optical intensity of the above beat signal on the basis of the interference light Lc, and detects the intensity of the measurement light Ls' reflected from a certain depth in the region to be observed, by heterodyne interferometry. The detected intensity of the reflected measurement light Ls' is outputted to the optical-tomographic-information generation unit 54.

When the wavelength of the measurement light Ls applied to the region to be observed is 750 nm, fluorescence having the wavelengths of 770 to 900 nm is emitted from the region to be observed. However, since such fluorescence is reflected by the dichroic mirror 48 toward the direction perpendicular to the direction in which the fluorescence is incident on the dichroic mirror 48, such fluorescence does not enter the optical detector 47a.

The optical-tomographic-information generation unit 54 generates optical tomographic information on the basis of the intensity of the reflected measurement light Ls', and outputs the optical tomographic information to the controller 52. Thereafter, the actuator 46 moves the reference-light mirror 45 in the direction of the optical axis of the reference-light mirror 45 (i.e., the horizontal direction), so that the optical path length of the reference light Lr along the path from the fiber coupler 39 via the optical-path delay unit 33 back to the fiber coupler 39 varies. At this time, the optical path length of the aforementioned portion of the measurement light Ls (as the reflected measurement light Ls') which interferes with the reference light Lr also varies, and therefore the depth in the region to be observed from which tomographic information is acquired varies. The depth is gradually varied, and the acquisition of the tomographic information is repeated. In this example, tomographic information at depths from zero to approximately 2 millimeters under each incident point of the light is acquired. The actuator 46 in the optical-path delay unit 33 is connected to the controller 52, at port "b" of the actuator 46 and port "b" of the controller 52, so that information on the optical path length is successively outputted to the controller 52.

When the acquisition of the optical tomographic information under each incident point of the light is completed, the direction of application of the measurement light Ls is changed (i.e., the incident point of the measurement light Ls is moved) by slightly rotating the rotatable sheath 12 by actuation of the centerless motor 22, and optical tomographic information under the moved incident point is acquired. Movement of the incident point of the measurement light Ls by a small amount and acquisition of the optical tomographic information under the moved incident point are repeated, so that radial scanning around the length axis of the optical fiber 15 is realized, and information for a radial optical tomographic image at a cross section of the region to be observed is obtained.

The controller 52 generates a radial optical tomographic image on the basis of the optical path length, the rotation angle of the centerless motor 22, and the optical tomographic information outputted from the optical-tomographic-information generation unit 54, and outputs the radial optical tomographic image to the monitor 70, which displays the radial optical tomographic image. For example, the radial optical tomographic image covers a portion of the region to be observed, at depths from zero to approximately 2 millimeters from a surface of the region, as illustrated in FIG. 2B. Although the resolution of the optical tomographic image varies with the wavelength and the coherent length of the low-coherence light emitted from the light source 36, it is possible to increase the resolution to several micrometers when necessary.

Next, operations for acquiring and displaying an ultrasound-modulated-light tomographic image and a fluorescence (ultrasound-modulated-fluorescence) tomographic image are explained below.

An ultrasound-actuation signal is oscillated in and outputted from the ultrasound-signal processing unit 51 under control of the controller 52, so that an ultrasonic wave is outputted from the ultrasonic transducer 13, and applied to the region to be observed. At the same time, low-coherence light is outputted from the light-source unit 31. Specifically, low-coherence light is emitted from the light source 36, and propagates through the optical fiber 41, the fiber coupler 39, and the optical fiber 42 toward the probe 10. Then, the low-coherence light enters the optical fiber 15 through the condensing lens 19, propagates through the optical fiber 15, is outputted from the tip of the optical fiber 15, and is applied to the region to be observed through the rod lens 17 and the mirror 18.

Since the ultrasonic wave, as well as the low-coherence light, is applied to the region to be observed, the ultrasonic wave causes an elastic wave (i.e., compression and rarefaction of tissue) in the region to be observed, and produces a distribution of the refractive index in the region, so that the light is modulated when the light propagates in the region to be observed. In this case, it is possible to acquire tomographic information from the region which is to be observed and to which the light is applied, by analyzing the modulated light (i.e., reflected light). Then, the ultrasound-modulated light reflected from the region which is to be observed and is influenced by the ultrasonic wave is returned to the optical fiber 42 through the mirror 18, the rod lens 17, the optical fiber 15, and the condensing lens 19, is condensed by the condensing lens 49, passes through the dichroic mirror 48, and enters the optical detector 47a, which detects the intensity of the ultrasound-modulated light.

The output of the optical detector 47a is supplied to the ultrasound-modulated-tomographic-information generation unit 55 under control of the controller 52. At this time, the ultrasound-actuation signal is also supplied from the ultrasound-signal processing unit 51 to the ultrasound-modulated-tomographic-information generation unit 55. The ultrasound-modulated-tomographic-information generation unit 55 generates ultrasound-modulated-light tomographic information on the basis of the ultrasound-actuation signal and the intensity of the reflected light detected by the optical detector 47a. Since the ultrasound-modulated-tomographic-information generation unit 55 is informed of the oscillation timing of the ultrasound-actuation signal, it is possible to acquire ultrasound-modulated-light tomographic information along a line extending from the surface of the region to a depth of approximately 5 to 10 millimeters in the region to be observed by only one operation of detecting the reflected light. In addition, since the resolution of the ultrasound-modulated-light tomographic image varies with the oscillation frequency of the ultrasonic wave, the degree of convergence of the light, and the like, it is possible to increase the resolution to tens of micrometers when necessary.

Further, since the region to be observed is doped in advance with the fluorescent agent, fluorescence having a wavelength in the range of 770 to 900 nm is emitted from the region to be observed when light is applied to the region to be observed. In addition, since the ultrasonic wave is also applied to the region to be observed, compression and rarefaction of the tissue are caused in the region to be observed. In this situation, when the fluorescence is emitted from the region to be observed, the fluorescence is influenced by the compression and rarefaction of the tissue, i.e., the fluorescence is modulated. Similarly to the aforementioned ultrasound-modulated (reflected) light, the modulated fluorescence (i.e., the ultrasound-modulated fluorescence) propagates through the optical fiber 15 and the optical fiber 42, and is condensed by the condensing lens 49. Since the ultrasound-modulated fluorescence belongs to the wavelength range of 770 to 900 nm, the ultrasound-modulated fluorescence is reflected by the dichroic mirror 48, and enters the optical detector 47b. The optical detector 47b detects the optical intensity of the ultrasound-modulated fluorescence, and outputs the detected optical intensity of the ultrasound-modulated fluorescence to the ultrasound-modulated-tomographic-information generation unit 55. The ultrasound-modulated-tomographic-information generation unit 55 generates fluorescence (ultrasound-modulated-fluorescence) tomographic information on the basis of the aforementioned ultrasound-actuation signal and the intensity of the ultrasound-modulated fluorescence detected by the optical detector 47b. Since the ultrasound-modulated-tomographic-information generation unit 55 is informed of the oscillation timing of the ultrasound-actuation signal, it is possible to acquire fluorescence (ultrasound-modulated-fluorescence) tomographic information along a line extending from the surface of the region to be observed to a depth of approximately 5 to 10 millimeters by only one operation of detecting the ultrasound-modulated fluorescence. In addition, the resolution of the ultrasound-modulated-light tomographic image varies with the oscillation frequency of the ultrasonic wave, the degree of convergence of the excitation light, and the like, it is possible to increase the resolution to tens of micrometers when necessary.

When the acquisition of the ultrasound-modulated-light tomographic information and the fluorescence (ultrasound-modulated-fluorescence) tomographic information under each incident point of the light is completed, the direction of application of the light is changed (i.e., the incident point of the light is moved) by slightly rotating the rotatable sheath 12 by actuation of the centerless motor 22, and ultrasound-modulated-light tomographic information and the fluorescence (ultrasound-modulated-fluorescence) tomographic information under the moved incident point is acquired. Movement of the incident point of the light by a small amount and acquisition of the ultrasound-modulated-light tomographic information and the fluorescence (ultrasound-modulated-fluorescence) tomographic information under the moved incident point are repeated, so that radial scanning around the length axis of the optical fiber 15 is realized, and ultrasound-modulated-light tomographic information and fluorescence (ultrasound-modulated-fluorescence) tomographic information at a cross section of the region to be observed is obtained.

The controller 52 generates a radial ultrasound-modulated-light tomographic image on the basis of the rotation angle of the centerless motor 22 and the ultrasound-modulated-light tomographic information outputted from the ultrasound-modulated-tomographic-information generation unit 55, and outputs the radial ultrasound-modulated-light tomographic image to the monitor 70, so that an ultrasound-modulated-light tomographic image, for example, as illustrated in FIG. 2C, is displayed on the monitor 70. In addition, the controller 52 also generates a radial fluorescence (ultrasound-modulated-fluorescence) tomographic image on the basis of the rotation angle of the centerless motor 22 and the fluorescence (ultrasound-modulated-fluorescence) tomographic information outputted from the ultrasound-modulated-tomographic-information generation unit 55, and outputs the radial fluorescence (ultrasound-modulated-fluorescence) tomographic image to the monitor 70, so that a fluorescence (ultrasound-modulated-fluorescence) tomographic image, for example, as illustrated in FIG. 2D, is displayed on the monitor 70. Thus, when the region to be observed contains a tumor, the position, size, and the like of the tumor are visualized in the fluorescence (ultrasound-modulated-fluorescence) tomographic image.

Further, the controller 52 can superimpose the ultrasound-modulated-light tomographic image and the fluorescence (ultrasound-modulated-fluorescence) tomographic image so as to generate a superimposed image, for example, as illustrated in FIG. 3, and instruct the monitor 70 to display the superimposed image. Since the ultrasound-modulated-light tomographic image and the fluorescence (ultrasound-modulated-fluorescence) tomographic image are concurrently acquired, the ultrasound-modulated-light tomographic image and the fluorescence (ultrasound-modulated-fluorescence) tomographic image can be easily aligned with each other. Therefore, the observer can concurrently recognize the cross-sectional profile of the region to be observed, the distribution of the fluorescent agent (indicating the position and the size of the tumor), and the like by observing the above superimposed image.

Hereinbelow, operations for acquiring and displaying a (radial) synthesized image are explained. In the synthesized image, an optical tomographic image, an ultrasound-modulated-light tomographic image, and an ultrasonic tomographic image are combined, and a fluorescence (ultrasound-modulated-fluorescence) tomographic image is superimposed on the combined tomographic image.

First, the four types of tomographic images (i.e., an optical tomographic image, an ultrasound-modulated-light tomographic image, a fluorescence (ultrasound-modulated-fluorescence) tomographic image, and an ultrasonic tomographic image) of the region to be observed are acquired. Although the four types of tomographic images may be acquired in separate scanning operations, alternatively, the four types of tomographic images can be acquired during a single turn of the rotatable sheath 12. That is, information for the four types of tomographic images is acquired while the rotatable sheath 12 is in each angular position in which the light and the ultrasonic wave is directed to an incident point on the region to be observed. Then, movement of the incident point on the region by a small rotation of the rotatable sheath 12 and acquisition of information for the four types of tomographic images under the moved incident point on the region are repeated until the rotatable sheath 12 rotates 360 degrees. Further, it is possible to acquire the ultrasonic tomographic information concurrently with the ultrasound-modulated-light tomographic information and fluorescence (ultrasound-modulated-fluorescence) tomographic information.

Figure 4A:
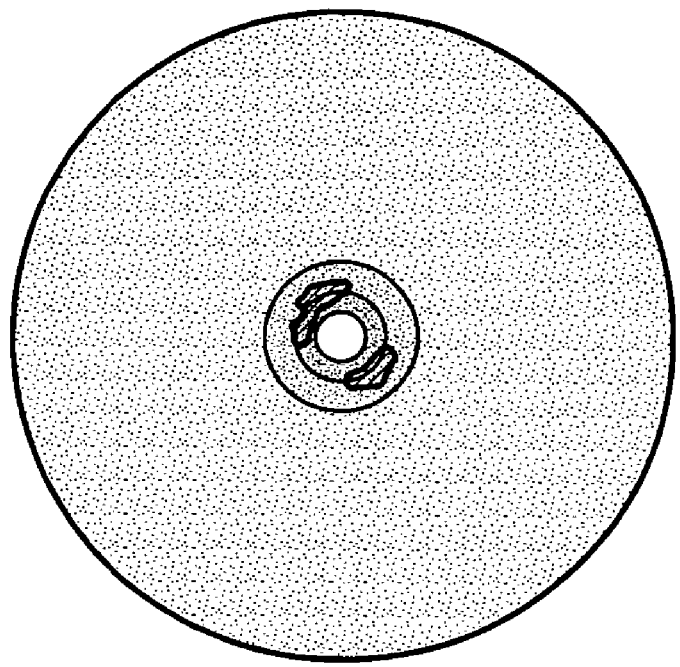
FIG. 4A is a diagram schematically illustrating an example of a synthesized tomographic image.
Figure 4B:
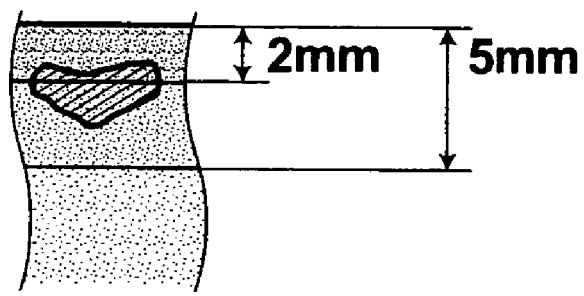
FIG. 4B is a diagram schematically illustrating a magnified image of a portion of the synthesized tomographic image of FIG. 4A.

After the four types of tomographic images are stored in a storage (not shown), the controller 52 acquires a small-depth tomographic image from the optical tomographic image (acquired by the aforementioned function of acquiring an optical tomographic image), a middle-depth tomographic image from the ultrasound-modulated-light tomographic image (acquired by the aforementioned function of acquiring an ultrasound-modulated-light tomographic image), and a great-depth tomographic image from the ultrasonic tomographic image (acquired by the aforementioned function of acquiring an ultrasonic tomographic image), and synthesizes the small-depth tomographic image, the middle-depth tomographic image, and the great-depth tomographic image, where the small-depth tomographic image is a tomographic image of a small-depth portion of the region to be observed, the middle-depth tomographic image is a tomographic image of a middle-depth portion of the region to be observed, and the great-depth tomographic image is a tomographic image of a great-depth portion of the region to be observed. For example, as illustrated in FIG. 4B, the small-depth portion extends from the surface of the region to be observed to a depth of approximately 2 millimeters, the middle-depth portion extends from the depth of approximately 2 millimeters to a depth of approximately 5 to 10 millimeters, and the great-depth portion extends from the depth of approximately 5 to 10 millimeters to a depth of 30 millimeters. Then, the controller 52 superimposes the fluorescence (ultrasound-modulated-fluorescence) tomographic image on the image generated by the above synthesis of the small-depth tomographic image, the middle-depth tomographic image, and the great-depth tomographic image so as to generate a synthesized tomographic image, and outputs the synthesized tomographic image to the monitor 70. The monitor 70 displays a radial, synthesized tomographic image, for example, as illustrated in FIG. 4A.

In the above synthesized tomographic image, the small-depth portion of the region to be observed is displayed by use of the optical tomographic image having a high resolution of several micrometers, the middle-depth portion of the region to be observed is displayed by use of the ultrasound-modulated-light tomographic image having a middle resolution of tens of micrometers, and the great-depth portion of the region to be observed is displayed by use of the ultrasonic tomographic image having a low resolution of hundreds of micrometers. Therefore, the observer can easily observe a profile and the like of the tissue. In addition, since the fluorescence (ultrasound-modulated-fluorescence) tomographic image is superimposed on the image generated by the above synthesis of the small-depth tomographic image, the middle-depth tomographic image, and the great-depth tomographic image, the observer can recognize the presence or absence, size, and the like of a tumor as well as the profile and the like of the tissue.

Further, it is possible to repeat the above radial scanning and the aforementioned linear scanning for acquiring a plurality of successive fluorescence (ultrasound-modulated-fluorescence) tomographic images, perform analytic processing, such as image restoration processing, of the plurality of successive fluorescence (ultrasound-modulated-fluorescence) tomographic images, generate a three-dimensional fluorescence (ultrasound-modulated-fluorescence) tomographic image, and display the three-dimensional fluorescence tomographic image on the monitor 70. In this case, the observer can observe more easily the condition of the region to be observed.

Advantages and Other Matters

As explained above, the fluorescence tomography apparatus according to the present embodiment has the functions of concurrently applying an ultrasonic wave and excitation light to a region to be observed, and acquiring an ultrasound-modulated-light tomographic image of the region on the basis of ultrasound-modulated fluorescence emitted from the region which is influenced by the ultrasonic wave. Therefore, it is possible to obtain a fluorescence tomographic image of a portion of the region which is to be observed and is located at depths of zero to several millimeters from a surface of the region, with a high resolution (up to tens of micrometers). For example, in the case where the region to be observed is doped in advance with a fluorescent agent having an affinity for a tumor, it is possible to recognize the position, size, and the like of the tumor by observing the fluorescence (ultrasound-modulated-fluorescence) tomographic image.

Although the radial synthesized tomographic image is generated in the above embodiment, it is possible to acquire the ultrasonic tomographic image, the optical tomographic image, the fluorescence (ultrasound-modulated-fluorescence) tomographic image, and the ultrasound-modulated-light tomographic image by linear scanning, generate a linear synthesized tomographic image on the basis of the ultrasonic tomographic image, the optical tomographic image, the fluorescence (ultrasound-modulated-fluorescence) tomographic image, and the ultrasound-modulated-light tomographic image, and display the linear synthesized tomographic image. Further, it is possible to combine radial scanning and linear scanning so as to acquire a three-dimensional ultrasonic tomographic image, a three-dimensional optical tomographic image, a three-dimensional fluorescence (ultrasound-modulated-fluorescence) tomographic image, and a three-dimensional ultrasound-modulated-light tomographic image by linear scanning, and generate a synthesized tomographic image on the basis of the three-dimensional ultrasonic tomographic image, the three-dimensional optical tomographic image, the three-dimensional fluorescence tomographic image, and the three-dimensional ultrasound-modulated-light tomographic image.

Although, in the present embodiment, the some constructions for acquisition of the respective types of tomographic images are arranged inside the probe, all or a portion of such constructions may be built in a portion of an endoscope which is inserted into a human body.

All of the contents of the Japanese patent application No. 2005-018347 are incorporated into this specification by reference.

What is claimed is:

1. A fluorescence tomography apparatus for obtaining fluorescence tomographic images of a region of an object to be observed, comprising:
   an application unit which concurrently applies a first ultrasonic wave and excitation light to said region so that ultrasound-modulated fluorescence is emitted from the region under the influence of the first ultrasonic wave, and applies a second ultrasonic wave and first light to said region so that said first light is reflected from the region under the influence of the second ultrasonic wave, and ultrasound-modulated reflected light is generated;
   a first image acquisition unit which acquires a fluorescence tomographic image of said region on the basis of said ultrasound-modulated fluorescence;
   a second image acquisition unit which concurrently with said acquisition of said fluorescence tomography image, acquires an ultrasound-modulated light tomographic image of said region on the basis of said ultrasound-modulated reflected light; and
   wherein said application unit applies second light to said region so that said second light is reflected from the region, and the fluorescence tomography apparatus further comprises:
   a third image acquisition unit which acquires an optical tomographic image of said region on the basis of said second light reflected from the region.

2. A fluorescence tomography apparatus according to claim 1, wherein said region is doped in advance with a fluorescent agent having an affinity for a tumor.

3. A fluorescence tomography apparatus according to claim 1, wherein said first image acquisition unit comprises a three-dimensional-image generation unit which generates a three-dimensional fluorescence tomographic image from a plurality of fluorescence tomographic images, which are acquired by said first image acquisition unit.

4. A fluorescence tomography apparatus according to claim 2, wherein said first image acquisition unit comprises a three-dimensional-image generation unit which generates a three-dimensional fluorescence tomographic image from a plurality of fluorescence tomographic images, which are acquired by said first image acquisition unit.

5. A fluorescence tomography apparatus according to claim 1, wherein
   said application unit applies a third ultrasonic wave to said region so that said third ultrasonic wave is reflected from the region, and the fluorescence tomography apparatus further comprises: a fourth image acquisition unit which acquires an ultrasonic tomographic image of said region on the basis of said third ultrasonic wave reflected from the region.

6. A fluorescence tomography apparatus according to claim 2, wherein
   said application unit applies a third ultrasonic wave to said region so that said third ultrasonic wave is reflected from the region, and the fluorescence tomography apparatus further comprises:
   a fourth image acquisition unit which acquires an ultrasonic tomographic image of said region on the basis of said third ultrasonic wave reflected from the region.

7. A fluorescence tomography apparatus according to claim 3, wherein
   said application unit applies a third ultrasonic wave to said region so that said third ultrasonic wave is reflected from the region, and the fluorescence tomography apparatus further comprises:
   a fourth image acquisition unit which acquires an ultrasonic tomographic image of said region on the basis of said third ultrasonic wave reflected from the region.

8. A fluorescence tomography apparatus according to claim 4, wherein
   said application unit applies a third ultrasonic wave to said region so that said third ultrasonic wave is reflected from the region, and the fluorescence tomography apparatus further comprises:
   a fourth image acquisition unit which acquires an ultrasonic tomographic image of said region on the basis of said third ultrasonic wave reflected from the region.

9. A fluorescence tomography apparatus according to claim 1, further comprising a rotatable sheath, through which said first ultrasonic wave, said excitation light, said second ultrasonic wave, said first light, and said second light are applied to said region.

10. A fluorescence tomography apparatus according to claim 9, wherein said fluorescence tomographic image and said ultrasound-modulated-light tomographic image are acquired during a single turn of said rotatable sheath.

11. A fluorescence tomography apparatus according to claim 1, further comprising a wavelength separation element which separates said ultrasound-modulated reflected light and said ultrasound-modulated fluorescence; wherein
   said second ultrasonic wave is said first ultrasonic wave and said first light is said excitation light.

12. A fluorescence tomography apparatus according to claim 1, wherein
   said application unit applies a third ultrasonic wave to said region so that said third ultrasonic wave is reflected from the region, and the fluorescence tomography apparatus further comprises:
   a fourth image acquisition unit which acquires an ultrasonic tomographic image of said region on the basis of said third ultrasonic wave reflected from the region, and
   a controller which acquires a small-depth tomographic image from the optical tomographic image, a middle-depth tomographic image from the ultrasound-modulated-light tomographic image, and a great-depth tomographic image from the ultrasonic tomographic image, synthesizes the small-depth tomographic image, the middle-depth tomographic image, and the great-depth tomographic image, wherein the small-depth tomographic image is a tomographic image of a small-depth portion of the region to be observed, the middle-depth tomographic image is a tomographic image of a middle-depth portion of the region to be observed, and the great-depth tomographic image is a tomographic image of a great-depth portion of the region to be observed, and superimposes the fluorescence image on the image generated by the above synthesis of the small-depth tomographic image, the middle-depth tomographic image, and the great-depth tomographic image.

13. A fluorescence tomography apparatus for obtaining fluorescence tomographic images of a region of an object to be observed, comprising:
   an application unit which concurrently applies a first ultrasonic wave and excitation light to said region so that ultrasound-modulated fluorescence is emitted from the region under the influence of the first ultrasonic wave and applies a second ultrasonic wave and first light to said region so that said first light is reflected from the region under the influence of the second ultrasonic wave, and ultrasound-modulated reflected light is generated;

a first image acquisition unit which acquires a fluorescence tomographic image of said region on the basis of said ultrasound-modulated fluorescence, and a second image acquisition unit which concurrently with said acquisition of said fluorescence tomography image, acquires an ultrasound-modulated light tomographic image of said region on the basis of said ultrasound-modulated reflected light, wherein said fluorescence tomography apparatus further comprises a rotatable sheath, through which said first ultrasonic wave, said excitation light, said second ultrasonic wave, and said first light are applied to said region.

* * * * *